United States Patent
Reifart et al.

(10) Patent No.: US 6,733,473 B1
(45) Date of Patent: May 11, 2004

(54) ADJUSTABLY STIFFENABLE CONVERTIBLE CATHETER ASSEMBLY

(75) Inventors: Nikolaus Reifart, Eppstein/Taunus (DE); Erik Andersen, Jvllinge (DK); John E. Abele, Concord, MA (US); Sandra G. Tartaglino, Canton, MA (US); Timothy W. Wheeler, Upton, MA (US)

(73) Assignee: Boston Scientific Corporation

( * ) Notice: Subject to any disclaimer, the term of this patent is extended or adjusted under 35 U.S.C. 154(b) by 0 days.

(21) Appl. No.: 08/089,655

(22) Filed: Jul. 9, 1993

Related U.S. Application Data

(63) Continuation of application No. 08/007,756, filed on Jan. 22, 1993, which is a continuation of application No. 07/681,805, filed on Apr. 5, 1991, now abandoned.

(51) Int. Cl.$^7$ ............................................. A61M 29/00
(52) U.S. Cl. .................................. 604/96.01; 606/194
(58) Field of Search ............................. 606/192–195; 604/93.01, 94.01, 95.01, 95.02, 95.03, 95.04, 95.05, 96.01, 102.01, 102.02, 102.03, 523, 524, 160, 767

(56) References Cited

U.S. PATENT DOCUMENTS

| | | |
|---|---|---|
| 2,657,691 A | 11/1953 | Nordstrom |
| 2,936,760 A | 5/1960 | Gants |
| 3,225,762 A | 12/1965 | Guttman |
| 3,757,768 A | 9/1973 | Kline |
| 3,766,924 A | 10/1973 | Pidgeon |
| 4,033,331 A | 7/1977 | Guss et al. |
| 4,236,521 A | 12/1980 | Lauterjung |
| 4,244,362 A | 1/1981 | Anderson |
| 4,289,128 A | 9/1981 | Rusch |
| 4,299,226 A | 11/1981 | Banka |

(List continued on next page.)

FOREIGN PATENT DOCUMENTS

| | | |
|---|---|---|
| DE | 3934-695 A1 | 4/1991 |
| FR | 591963 | 4/1925 |
| SU | 1251914 | 5/1984 |
| WO | WO 92/20397 | 11/1992 |
| WO | WO 94/04216 | 3/1994 |

OTHER PUBLICATIONS

Nordenstrom; New Instr. for Catherization and Angiocardiography; *Radiology*, vol. 65, Jul.–Dec. 1965.

Nordenstrom; Balloon Catheters for Percotaneous Insertion; Mar. 1962, Dept. of Roentgenology; Stockholm, SW.

J. Simpson et al., A New Catheter System for Coronary Angioplasty, 49 Am. J. Cardiology, pp. 1216–1222 Apr. 1982.

*Primary Examiner*—Manuel Mendez
(74) *Attorney, Agent, or Firm*—Fish & Richardson P.C.

(57) ABSTRACT

A stiffenable balloon catheter assembly capable of being converted from an "over-the-wire" mode with respect to a guidewire extending therethrough to a "rapid-exchange" mode with respect to a guidewire extending therethrough, and vice versa. The catheter has a plurality of lumens, one lumen however, having a side opening with an obstructable galp, the orientation of which, determines the utilization "mode" of the catheter assembly. Stiffening stylets may be adjustably locked into the lumens, depending upon the "mode", to control the stiffness of the catheter assembly during its utilization within a patient.

65 Claims, 3 Drawing Sheets

U.S. PATENT DOCUMENTS

| | | |
|---|---|---|
| 4,413,989 A | 11/1983 | Schjeldahl et al. |
| 4,448,195 A | 5/1984 | LeVeen et al. |
| 4,516,972 A | 5/1985 | Samson |
| 4,545,390 A | 10/1985 | Leary |
| 4,552,554 A | 11/1985 | Gould |
| 4,581,017 A | 4/1986 | Sahota |
| 4,586,923 A | 5/1986 | Gould et al. |
| 4,737,152 A | 4/1988 | Alchas |
| 4,738,667 A | 4/1988 | Galloway |
| 4,771,777 A | 9/1988 | Horzewski et al. |
| 4,822,345 A | 4/1989 | Danforth |
| 4,824,435 A | 4/1989 | Giesy et al. |
| 4,875,481 A | 10/1989 | Higgins |
| 4,892,519 A | 1/1990 | Songer |
| 4,932,413 A | 6/1990 | Shockey et al. |
| 4,944,745 A | 7/1990 | Sogard et al. |
| 4,947,864 A | 8/1990 | Shockey et al. |
| 4,955,895 A | 9/1990 | Sugiyama et al. |
| 4,960,411 A | 10/1990 | Buchbinder |
| 4,964,853 A | 10/1990 | Sugiyama et al. |
| 5,040,548 A | 8/1991 | Yock |
| 5,102,403 A | 4/1992 | Alt |
| 5,135,535 A | 8/1992 | Kramer |
| 5,154,725 A | 10/1992 | Leopold |
| 5,156,594 A | 10/1992 | Keith |
| 5,195,971 A | 3/1993 | Sirhan |
| 5,195,978 A | 3/1993 | Schiffer |
| 5,205,822 A | 4/1993 | Johnson et al. |
| 5,217,482 A | 6/1993 | Keith |
| 5,232,445 A | 8/1993 | Bonzel |
| 5,290,232 A | 3/1994 | Johnson et al. |
| 5,300,085 A | 4/1994 | Yock |
| 5,324,269 A | 6/1994 | Miraki |
| 5,364,376 A | 11/1994 | Horzewski et al. |
| 5,389,087 A | 2/1995 | Miraki |

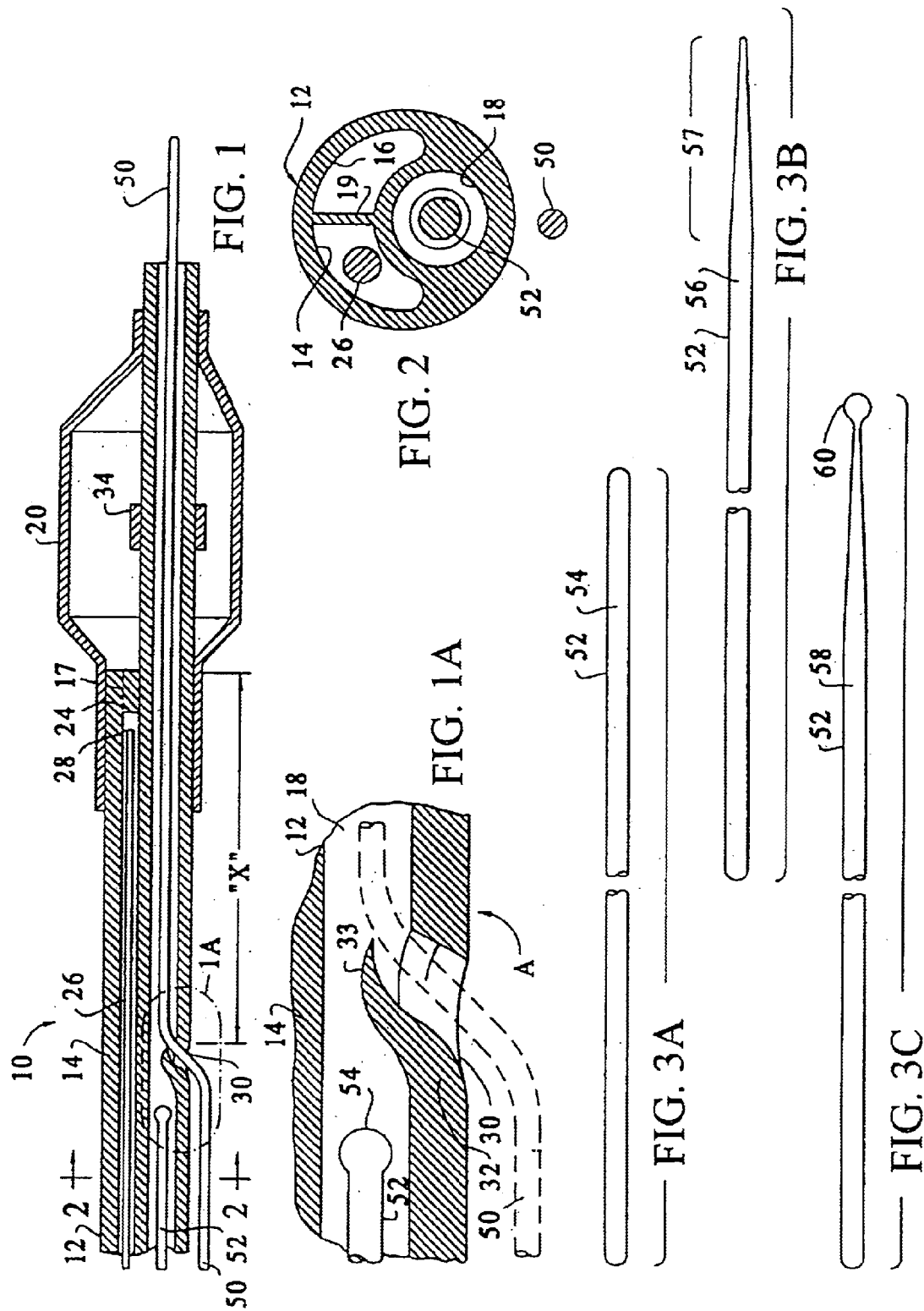

ADJUSTABLY STIFFENABLE CONVERTIBLE CATHETER ASSEMBLY

CROSS-REFERENCE TO RELATED APPLICATION

This is a continuation of application Ser. No. 08/007,756, filed Jan. 22, 1993, which was a continuation of application Ser. No. 07/681,805, filed Apr. 5, 1991 now abandoned.

BACKGROUND OF THE INVENTION

1. Field of the Invention

This invention relates to a catheter having a balloon at its distalmost end, and having means for adjustably controlling the stiffness of the catheter shaft, and more particularly to a convertible-type balloon catheter having stiffener means disposed within the catheter.

2. Prior Art

Balloon catheters are utilized for insertion into the human body into lumens therewithin. The catheters are of necessity made of a flexible plastic extrusion such as polyethelene, polyester or polyamide. Advancement and manipulation of a catheter requires a certain stiffness or pushability of the catheter itself, by the physician, without injuring the patient in which the catheter is placed.

A number of approaches have been made, in attempting to provide stiffness to catheters. U.S. Pat. No. 4,964,853 to Sugiyama et al shows a balloon catheter having a braided wire member disposed within the catheter body itself in a mesh-like manner. Mesh is imbedded in the wall of the inner tube. U.S. Pat. No. 4,875,841 to Higgins shows a balloon catheter having a coiled wire arranged within the proximalmost hub, which coiled wire extends in an uncoiled manner within the body of the catheter shaft itself. The coil and the wire itself being co-rotatable so as to provide rotational stiffness to the catheter.

U.S. Pat. No. 4,822,345 to Danforth shows a variable stiffener balloon catheter, for percutaneous transluminal coronary angioplasty procedures. This patent to Danforth shows a method of providing for variable flexibility, by the use of a longitudinally extended balloon arranged along the exterior of the catheter shaft. Pressurization or depressurization of this balloon is effectuated by a syringe, which pressurizably controls the rigidity of the balloon itself. A further embodiment of this concept of Danforth utilizes relatively stiff wires running through channels in the periphery of the catheter, the wires adding the stiffness to the catheter.

The preformed catheter assembly shown in U.S. Pat. No. 4,738,667 to Galloway discloses a sheath which is slideably mounted over the catheter so as to be moved from the proximal to the distal end, to straighten out the distal end during insertion and removal of the catheter from a body. The catheter assembly shown in U.S. Pat. No. 4,737,152 to Alchas shows a stylet or stiffening wire arranged within a lumen connected to the closed distal end of the catheter and also there is a loop on its proximalmost end. The loop is arranged in a rotatable knob to facilitate rotation of the distal end of the catheter while providing stiffness, while the proximal end is turned.

U.S. Pat. No. 4,586,923 issued to Gould et al shows a curving tip catheter having a catheter body which includes a sheath of braided wire having a meshlike configuration positioned around the wall of the tubular body to provide tortional stiffness to the body relative to the flexible tip. In an alternative embodiment, a relatively stiff but bendable inner plastic tubing can be inserted within the tubular body to provide tortional stiffness to that body. In a somewhat similar vein, U.S. Pat. No. 4,516,972 to Sampson shows a guiding catheter having a helically wound ribbon of flexible material embedded within the wall of the catheter, so as to provide tortional rigidity and stiffness.

In yet a further embellishment on the idea of stiffening a balloon catheter, U.S. Pat. No. 4,448,195 to LeVeen et al shows a reinforced balloon catheter which has a guidewire adapted to be inserted for stretching the catheter when it is inserted into a blood vessel to stiffen the catheter and position it. In an alternative arrangement, a braided shell wire reinforcement is used within the braids, which are placed at the beginning and endings of the thinned portion of the catheter. U.S. Pat. No. 4,033,331 to Guss et al, discloses a contour or stiffening wire slideably disposed within a lumen extending substantially the full length of the catheter. Slight retraction of the stiffening wire from the distal end of the lumen permits catheter to assume a predetermined curvature thereat.

It is thus an object of the present invention to provide a catheter having variable stiffness capabilities therewithin. The catheter of the present invention should overcome the problems of the prior art by getting the physician to properly adjust the rigidity or stiffness of the catheter shaft according to the particular situation that warrants it in conjunction with the capability of utilizing the catheter shaft in a convertible manner between a "rapid-exchange" mode and an "over-the-wire" mode.

Angioplasty "over-the-wire" balloon catheters are known. Simpson et al., U.S. Pat. No. 4,323,071 describes a percutaneous transluminal coronary angioplasty (PTCA) dilatation catheter that is advanced through the vasculature of a patient over a previously inserted guidewire that is threaded through a guidewire lumen that extends the full length of the catheter.

"Rapid-exchange" balloon catheters are also known. Bonzel, U.S. Pat. No. 4,762,129 describes a dilatation catheter in which a short sleeve extends through the balloon and is sealed off from the interior of the balloon. The sleeve has a guidewire lumen extending therethrough. A permanently imbedded stabilizing wire, that makes the catheter by itself pushable without the use of a removable stiffener or stylet, extends the entire length of the catheter to the distal end of the balloon. Yock, U.S. Pat. No. 5,061,273 describes a rapid-exchange angioplasty catheter having a short guidewire lumen though greater than 10 cm in length, extending through the balloon and through a portion of the catheter shaft proximal of the balloon.

Horzewski et al., U.S. Pat. No. 4,748,982 describe a rapid-exchange catheter having, in manufacture, a passage extending through the full length of the catheter. A port is located in the side of the catheter shaft some distance from the distal end of the catheter. A distal portion of the passage extending from this port, through the balloon, functions as a guidewire passage. A slit extends longitudinally from the port in the side of the catheter shaft to a region adjacent the balloon, permitting the guide wire to be removed therethrough. A permanent plug blocks the passage immediately proximal of the port in the side of the catheter shaft. A stainless steel stiffener mandrel that is tapered at its distal end is provided in the portion of the lumen that is proximal of the plug.

Crittenden et al., U.S. Pat. No. 4,988,356 and Euteneur et al., U.S. Pat. No. 5,171,222, teach catheters capable of both over-the-wire and rapid-exchange modes of operation, but without use of a side port to receive a guidewire. Both of these patents disclose a catheter having a guidewire lumen extending through the full length of the catheter and having a slit extending from a location near the proximal end of the catheter shaft to a distal location located proximal of the balloon. The slit enables a guidewire to be stripped from the catheter shaft through the slit or merged into the slit.

BRIEF SUMMARY OF THE INVENTION

The present invention comprises a balloon catheter having a catheter shaft with at least three lumens extending from the proximal to the distal ends thereof. The first and second lumens may preferably but not necessarily be of cresent shape in cross-section, and the third lumen is of circular cross-section. At least one of the cresent shaped lumens has a stiffening mandrel extending therethrough. In a preferred embodiment, the third lumen has a side opening arranged relatively close yet proximal to the balloon at the distal end of the catheter assembly.

The balloon on the distal end of the catheter shaft is in fluid communication with one of the cresent shaped lumens. The first shaped lumen has a closed distalmost end, at the proximal end of the balloon.

The third lumen, preferably of circular cross-section, extends from the proximal end of the catheter shaft, and through the balloon, open at its distalmost end at the distal end of the balloon. The third lumen is adapted to receive a guidewire, either through the entire length thereof, or from an opening proximal of the balloon and through to its distalmost end.

In a preferred embodiment, a guidewire is adaptable to enter the third "distal" lumen at its opening at the distalmost end of the catheter and extend through that lumen, through the balloon, and exit out the side opening through the sidewall of the catheter, proximal of the balloon. The side "guidewire" opening of the third lumen being disposed through the wall of the catheter shaft at a location which is also proximal to the distal end of the stiffening mandrel in the first cresent shaped lumen. This rapid exchange mode with a guidewire extending partway through may occur with a stiffening stylet disposed within the third lumen, the stylet extending up to a location adjacent the side opening, from the proximal end of the catheter. This same lumen, a portion of which is utilized for the "rapid-exchange" mode, is utilized in its entire length, for the catheter in its "over-the-wire" mode, where a guidewire enters the distal opening of the third "distal" lumen, and exits at the proximal end of the catheter at the proximal end of that third lumen, through a connector or adaptor.

The present invention thus comprises a multiple lumen catheter (at least three lumens) having proximal and distal ends, the proximal end having a Y-connector thereat for adaptation of inflation devices or control functions, the distal end comprising an inflatable elongated balloon.

A first of the lumens has an elongated stiffening mandrel disposed therein, the lumen being closed at its distalmost end. The stiffening mandrel being preferably made of Nitinol. A second of the lumens extending from the connector, and into the balloon, providing fluid communication therewith. The third of the lumens being preferably circular in cross-section, extending from the connector and through the balloon, and open through the distal tip of the catheter shaft. A "side" orifice being disposed through the wall of the catheter and into the third lumen, just proximal (about 15 to 35 cm) of the balloon. The stiffening mandrel in the first lumen extending distally of the side orifice in the third lumen to the proximal end of the catheter, so as to allow a smoother transition of catheter stiffness when the assembly is utilized in a rapid exchange mode—that is, when a guidewire extends only part way through the third lumen, out through the "side" orifice after entering that lumen distally and to help transmit "push" on the catheter shaft from its proximal end. The same lumen therefore, in the same catheter, functioning as a lumen for an "over-the-wire" mode, as well as a "rapid-exchange-wire" mode, using part of the lumen for a guidewire and part of that lumen for catheter stiffening assistance.

BRIEF DESCRIPTION OF THE DRAWINGS

The objects and advantages of the present invention will become more apparent when viewed in conjunction with the following drawings, in which:

FIG. 1 is a sectional side-elevational view of the distal portion of a catheter assembly constructed according to the principles of the present invention;

FIG. 1a is an enlarged view of the "side opening" shown in cross-section in FIG. 1;

FIG. 2 is a cross-sectional view taken along the lines II—II of FIG. 1;

FIGS. 3a, 3b, and 3c are side-elevational views of stiffening mandrels contemplated with this catheter assembly;

DESCRIPTION OF THE PREFERRED EMBODIMENTS

Figure 4:
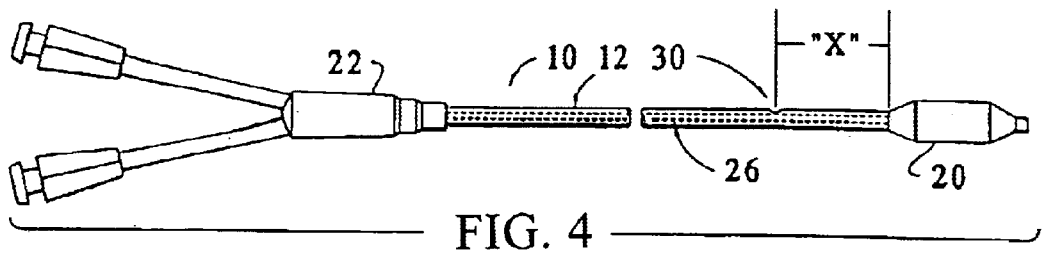
FIG. 4 is a side-elevational view of a catheter assembly showing a bifucated connector therewith.

Referring to the drawings now in detail, and particularly to FIG. 1, there is shown the distal portion of a catheter assembly 10, also shown in its extended most form in FIG. 4. The catheter assembly 10 comprises an extruded catheter shaft 12 having a plurality of lumens disposed axially therethrough. The catheter shaft 12 has a first lumen 14, and a second lumen 16, both of which are preferably, but not necessarily of cresent shape, as shown in the cross-sectional view of FIG. 2. The catheter shaft 12 also includes a third lumen 18, which is preferably of circular cross-section.

The catheter shaft 12 has an elongated balloon 20 disposed about its distalmost end, in a known manner. The first lumen 14 extends from an opening, not shown, in a connector 22, shown in FIG. 4, distally towards a closed end 24, at the proximal end of the balloon 20. A stiffening mandrel 26, as shown in FIG. 1, is disposed within the length of the first lumen 14. The stiffening mandrel 26 may have a ball welded tip 28 or be otherwise tapered and flexible on its distalmost end, to prevent puncture of the lumen 14 by the mandrel 26. The stiffening mandrel is made from a metal wire selected from the group consisting of stainless steel or Nitinol.

The second lumen 16 extends from the connector 22, through the shaft 12, parallel to the first lumen 14, except that the second lumen 16 is in fluid communication with the balloon 20, as shown in phantom lines 17, in FIG. 1. The second lumen 16 provides a conduit for pressurized fluid for inflating and deflating the balloon 20 from an inflation/deflation device, not shown, which would be adaptable to the connector 22. It is to be noted that the view of FIG. 1 is sectioned to show the first lumen 14 and the third lumen 18, and not longitudinally bisect the web of material 19 separating the first and second lumens 14 and 16.

The third lumen 18, of generally circular cross-section, extends from the connector 22, through the shaft 12, and through the balloon 20, opening distally of the balloon 20, as shown in FIGS. 1 and 1A. The third lumen 18 is not in fluid communication with the balloon 20.

An opening or side orifice 30 is disposed through the wall of the catheter shaft 12, and into the third lumen 18, as shown in FIG. 1. The side opening 30 in this preferred embodiment is preferably a slightly oval opening of about 3 mm long and 0.5 mm wide, arranged at a sharp angle "A" of about 20 to about 60 degrees with respect to the longitudinal axis of the shaft. The side opening 30 includes a valve-like cover flap 32, integral with the shaft 12 with a distally tapering edge 33, the flap 32 being about the size to cover the opening 30, and is resilient so as to allow it flex over the opening 30, and within the third lumen 18, obstructing it somewhat, depending upon how the flap 32 is being biased. The side opening 30 is disposed a distance "x" of about 15 to about 35 cm. from the proximal end of the inflated balloon 20, as shown in FIGS. 1 and 4. The third or "distal" lumen 18 may thus be utilized in its entire length, from the proximal connector 22 to its distalmost orifice, for receiving a guidewire in an "over-the-wire" mode, the flap 32 roughly covering the inside of the opening 30. The lumen 18 may also be utilized, from the opening 30 to its distal end, in a "rapid-exchange-wire" mode with a guidewire extending through the distal end of the third lumen 18 and out the opening 39 once the flap 32 is flexed out of the way.

An RO (radio opaque) marker band 34 is disposed about the catheter shaft 12, (essentially the structure comprising the third lumen 18), at the mid-point of the balloon 20 in either the "over-the-wire" mode or the "rapid-exchange" mode.

Figure 6:
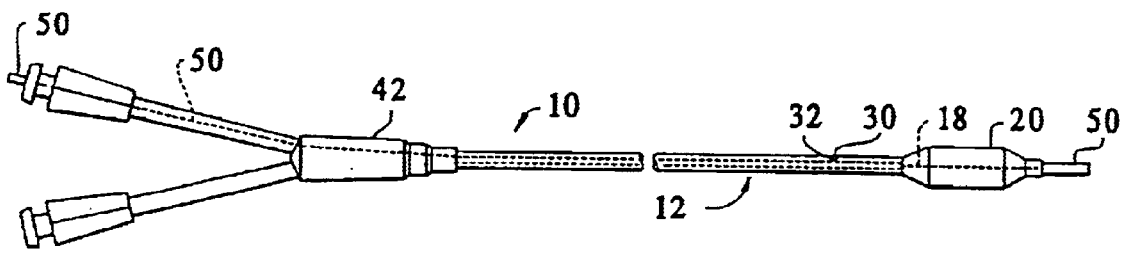
FIG. 6 is a side-elevational view of the catheter assembly in an "over-the-wire" mode.

In one embodiment of the present invention, where the catheter assembly 10 is utilized as aforementioned in the traditional "over-the-wire" catheter, a guidewire 50, normally initially having been inserted into a patient's vessel, and having its proximal end outside of the patient, has that proximal end inserted through the distal end of the catheter assembly 10, through the "distal" or third lumen 18, and it extends proximally, out of the proximal guidewire connector 42, as shown in FIG. 6. The flap 32 performs basically like a valve, by shutting itself against the opening 30, thus permitting an unobstructed lumen for passage of the guidewire 40, or for passage of pressurized fluid injected proximally in the lumen 18 to pass through the lumen 18, to escape primarily out of the distal end of the catheter shaft 12 through the lumen 18.

Figure 7:
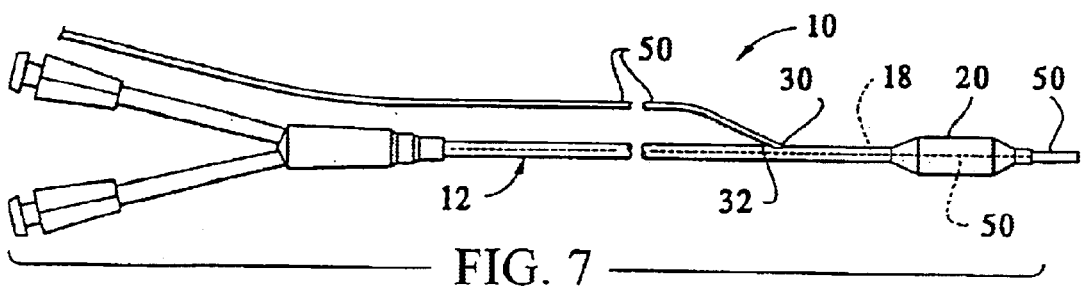
FIG. 7 is a side-elevational view of the catheter assembly in a "rapid exchange mode" configuration.

In a further embodiment of the present invention, where the catheter assembly 10 may be utililized in the aforementioned "rapid-exchange" mode, the guidewire 50, normally initially inserted into a patient's vessel, and having its proximal end outside of the patient, has that proximal end inserted through the distal end of the catheter assembly 10, through the "distal" lumen 18, and extending outwardly proximally, through the side opening 30 as shown in FIGS. 1 and 7. The guidewire 50 in this mode, extends parallel to and external of the shaft 12, proximal of the side opening 30. The enlarged view in FIG. 1A depicts the guidewire 50 shown in phantom lines, and the flap 32 in close fitting overlapping relationship to the guidewire 50. During the threading of the guidewire through the distal lumen 18, it is anticipated that the shaft 12 would be bent into a "U" shape at the opening 30, with the opening 30 in the trough of the "U", so as to cause the flap 32 to bend "away" from the opening 30, obstructing the lumen 18 proximally therepast to permit the guidewire 50 to be threaded through the lumen 18 and out the opening 30.

Additionally, when the catheter assembly 10 is utilized in this "rapid-exchange" mode, a stiffening stylet 52 may be inserted within the "distal" or third lumen 18 through the connector 22, as shown in FIGS. 1, 1A and 2. The stiffening stylet 52 has a distal end 54 which would extend only up to the side opening 30, and no further. The stiffening stylet 52 may have several different configurations, such as shown in FIG. 3A, 3B or 3C. The stylet 52 shown in FIG. 3A, is a straight mandrel 54, having uniform diameter along its entire length. The stylet 52 shown in FIG. 3B, is a tapered mandrel 56, having an initial diameter (its non-tapered end) of about 0.020 inches, and tapering about 5 cm. or more along its distal length 57 to a diameter of about 0.008 inches. The stylet 52 shown in FIG. 3C is a tapered mandrel 58, similar to the mandrel 56 shown in FIG. 3B, but having a ball weld 60 therein, of a diameter of about 0.020 inches. Each stylet 52 may be made from a stainless steel or Nitinol material, in a known manner.

Figure 5:
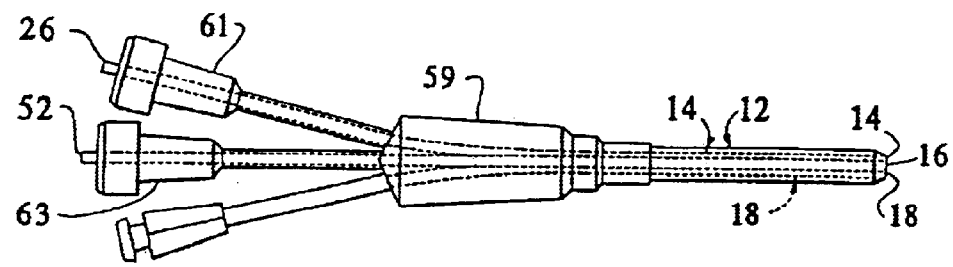
FIG. 5 is a side-elevational view of the proximal end of the catheter assembly showing a trifurcated connector therewith.

It is critical to the present invention that the location of the distalmost end of the stiffening mandrel 26 emplaced within the first lumen 14, as shown in FIG. 1 be juxtaposed distal to the location of the side hole 30 in the distal lumen 18 of the shaft 12. FIG. 5 shows a trifurcated connector 59 mounted on the proximal end of a catheter shaft 12 having a locking hub 61 which would be arranged to adjustably lock at stiffening stylet 26 within the first lumen 14 if desired. A further locking hub 63 may be arranged off of the connector 59 to adjustably seize a stiffening mandrel 52 in the third lumen 18 for longitudinal adjustment thereof, at the physicians option, while the catheter is being utilized in the "rapid-exchange" mode.

Figure 8:
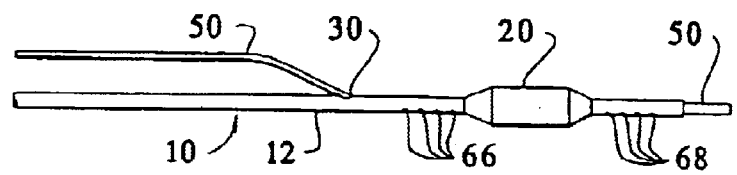
FIG. 8 is a side-elevational view of the catheter assembly in a further embodiment thereof.

FIG. 8 shows a further adaptation of the catheter assembly 10, wherein a plurality of orificii 66 is disposed through the wall of the catheter sheath 12 to provide fluid communication with the distal lumen 18 from the outside of the catheter shaft 12 at a location proximal of the balloon 20, and distal of the side hole 30. The orificii 66 are about 0.025 inches in diameter, and function as openings for passive perfusion. A further similar plurality of orificii 68 is disposed through the wall of the sheath 12 and distal of the balloon 20, to provide fluid communication with the distal lumen 18, to function as openings for passive perfusion with respect to that lumen 18.

Figure 9:
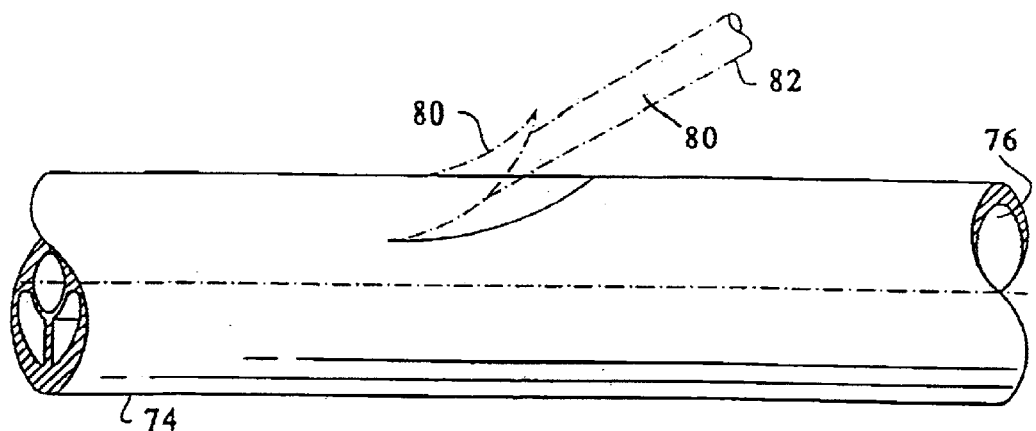
FIG. 9 is a side view of a part of a catheter shaft, in a further embodiment of the side opening.
Figure 10:
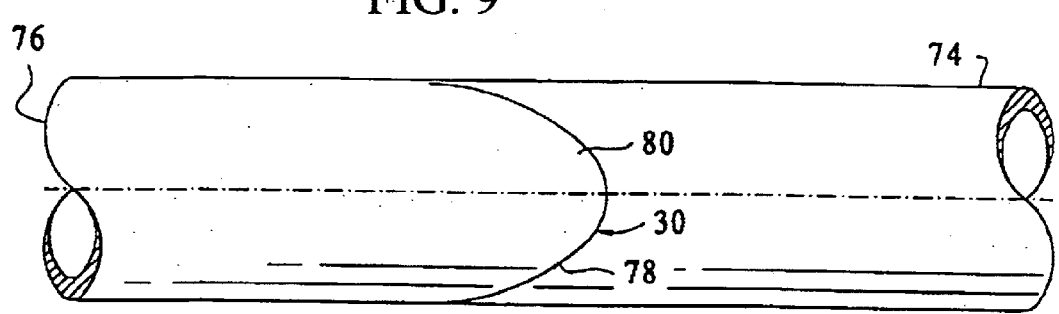
FIG. 10 is a plan view of the opening shown in FIG. 9.

A further embodiment of the side hole 30 is shown in FIG. 9, wherein a portion of a catheter shaft 74 has a "distal" lumen 76 extending therethrough, in a manner similar to the aforementioned catheter shaft 12. A slit 78 is cut diagonally through the outer wall of the catheter shaft 74, making a flap 80, which when flexibly lifted away from the lumen 76 provides a "D" shaped opening, through which a guidewire 82 may be passed. FIG. 10 shows the flap 80 in its "at rest" configuration, with the "D" shaped opening closed, to provide a full passage lumen 76 thereadjacent.

Figure 11:
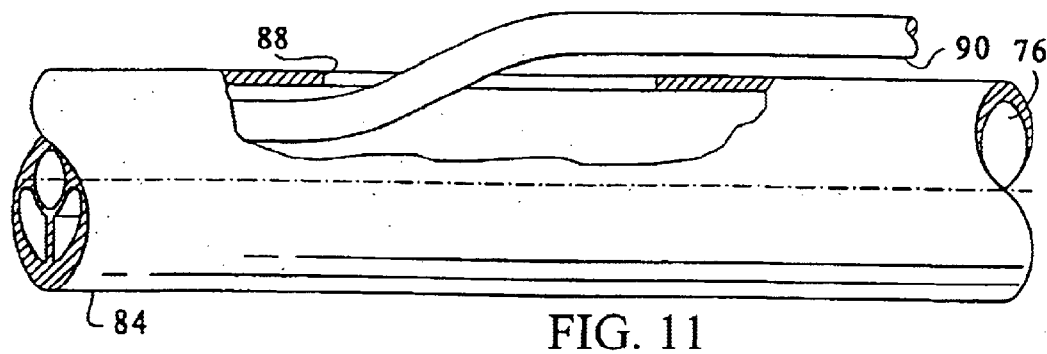
FIG. 11 is a side view of part of a catheter shaft in yet a further embodiment or the side opening.
Figure 12:
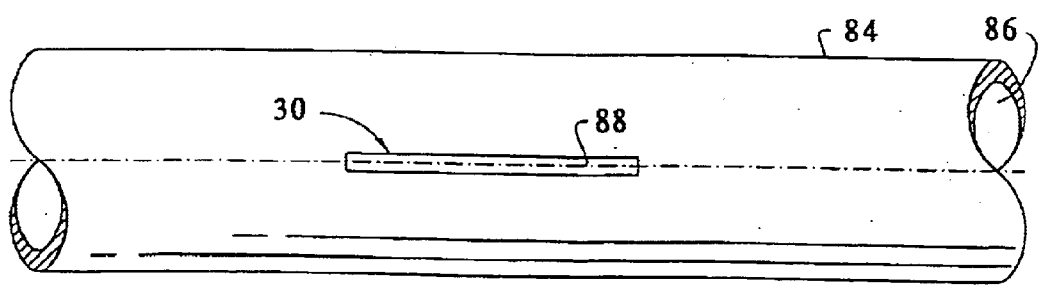
FIG. 12 is a plan view of the opening shown in FIG. 11.

A yet another embodiment of the side hole 30 is shown in FIG. 11, wherein a portion of a catheter shaft 84 has a "distal" lumen 86 extending therethrough. A slot 88 about 2 cm. long and 0.05 cm wide is diposed longitudinally through the outer wall of the catheter shaft 84, to make a flexibly openable orifice which a guidewire 90 may be passed. FIG. 12 shows the slot 38 in a plan view, in its "at rest" configuration.

Thus what has been shown is a novel stiffened catheter assembly 10 capable of being utilized by a physician as an "over-the-wire" catheter with adjustable stiffness means therewith, or optionally as a "rapid-exchange-wire" catheter apparatus, also including the capability of being able to control or vary the stiffness of the catheter shaft by selective insertion and/or controlled withdrawal of a stiffening stylet adaptably arranged within the guidewire lumen, the "rapid-exchange-wire" mode being facilitated by a side opening having valve-like obstructable flap across its inner side to minimize fluid exchange when that lumen accepts the catheter to be utilized in its full length "over-the-wire" mode. In its use as either a "rapid-exchange-wire" or an "over-the-wire" mode, the portion of the "distal" lumen enclosing the guidewire may have a plurality of orificii through the wall of the catheter shaft just proximal and just distal of the elongated inflated balloon, to permit perfusion of body fluid across the then expanded balloon in the body vessel.

We claim:

1. A catheter assembly for insertion within a body vessel, said catheter assembly capable of being converted between an "over-the-wire" mode and a "rapid-exchange-wire" mode through a common lumen in said catheter assembly, comprising:

an elongated extruded flexible shaft having a proximal end and a distal end, said shaft having a balloon arranged about said distal end and a connector arranged at said proximal end;

a first and a second lumen arranged within said shaft, said second lumen being in fluid communication with the interior of said balloon for the enablement of inflation and deflation thereof; and a third lumen extending between said proximal and distal ends of said shaft, said third lumen having means therewith to facilitate oversion of said catheter between an "over-the-wire" mode and a "rapid-exchange-wire" mode with a guidewire arrangeable through at least a portion of said third lumen.

2. A catheter assembly for insertion within a vessel as recited in claim 1, wherein said first lumen has a closed distal end arranged within said shaft, said first lumen being arranged to receive a stiffening means therein.

3. A catheter assembly for insertion within a vessel as recited in claim 1, wherein said means to facilitate conversion of said catheter from the "over-the-wire" mode to the "rapid-exchange-wire" mode in said third lumen comprises a side opening disposed through the wall of said shaft, opening into said lumen to permit a guidewire to pass therethrough.

4. A catheter assembly for insertion within a vessel as recited in claim 3, wherein said side opening is disposed in said shaft at a location proximal to said balloon on said shaft.

5. A catheter assembly for insertion within a vessel as recited in claim 3, wherein said side opening has a resilient flap extending thereacross, and within said lumen, to act as a valve to minimize fluid leakage with respect to said lumen when said catheter is in said "over-the-wire" mode.

6. A catheter assembly for insertion within a vessel as recited in claim 2, wherein said stiffening means within said first lumen comprises a metal stiffening mandrel.

7. A catheter assembly for insertion within a vessel as recited in claim 6, wherein said stiffening mandrel is made from a metal wire selected from the group consisting of stainless steel or Nitinol.

8. A catheter assembly for insertion within a vessel as recited in claim 6, wherein said stiffening mandrel has a distalmost end which is emplaced within said catheter shaft, said stiffening mandrel extending adjacent said side opening distal to the position of said side opening in said catheter shaft, to minimize kinking within said shaft.

9. A catheter assembly for insertion within a vessel as recited in claim 8, wherein said stiffening mandrel is axially displaceable in said first lumen so as to effect the rigidity of said catheter shaft therealong.

10. A catheter assembly for insertion within a vessel as recited in claim 9, wherein said first lumen has a blocking means on its proximal end, to engage said stiffening mandrel and prevent axial displacement therewith.

11. A dilatation catheter made from a shaft of extrudable flexible material having proximal and distal ends, said catheter having an expandable elongated balloon disposed about its distal end;

a first lumen disposed in said shaft, extending from said proximal end of said shaft, and having a closed end near the distal end of said shaft;

a second lumen disposed in said shaft and having a distal end thereof which is in fluid communication with said expandable balloon on the distal end of the said shaft;

a third lumen disposed in said shaft comprising a tubular wall, extending from said proximal end of said shaft, through said balloon, said lumen having a terminal distal end which is open distally of said balloon;

a stiffening means disposed within said first lumen;

an obstructed opening arranged through said wall of said third lumen to provide access for a guidewire through the said lumen distally therepast.

12. A dilatation catheter as recited in claim 11 wherein said obstructed opening comprises a flexible flap, integral with said wall, disposed across said opening to permit said lumen to receive a guidewire through its full length thereof.

13. A dilatation catheter as recited in claim 12, wherein said opening is disposed through said lumen wall, at an acute angle with respect to the longitudinal axis of said shaft.

14. A dilatation catheter as recited in claim 11, wherein said third lumen is adaptable to receive a stiffening stylet and a guidewire therein, simultaneously.

15. A dilatation catheter as recited in claim 11, wherein said stiffening means in said first lumen comprises at least one stiffening mandrel extendable within said lumen.

16. A dilatation catheter as recited in claim 15, wherein said first lumen has a mandrel locking means at its proximal end thereof, to permit selective adjustment and engagement of said stiffening mandrel therein.

17. A dilatation catheter as recited in claim 15, wherein said closed end of said first lumen is disposed distally on said shaft, with respect to said obstructed opening, so that when said stiffening mandrel is fully emplaced therein, said mandrel provides stiffness and resistance to kinking of said shaft fully across said obstructed opening.

18. A dilatation catheter from a shaft of extrudable flexible material having a distal and a proximal end shaft, said having an elongated expandable balloon disposed about its distal end;

a first lumen disposed in said catheter shaft, open at said proximal end, and closed at said distal end, proximal of said balloon, said first lumen adapted to receive a stiffening mandrel therein;

a second lumen disposed in said catheter shaft, open at said proximal end, and having its distal end in fluid communication with said balloon; and a third lumen disposed in said catheter shaft, said third lumen having a means for converting said dilatation catheter between an over-the-wire mode an da rapid-exchange-wire mode.

19. A dilatation catheter as recited in claim 18, wherein said third lumen is adaptable to receive a stiffening stylet and a separate guidewire therein, simultaneously.

20. A dilatation catheter as recited in claim 19, wherein said stiffening stylet and said separate guidewire are coaxial while both are in said third lumen.

21. A dilatation catheter as recited in claim 18, wherein said means for converting said catheter from an over-the-wire mode to a rapid-exchange mode comprises an acutely disposed opening arranged through the sidewall of said shaft, and in communication with said third lumen.

22. A dilatation catheter as recited in claim 18, wherein a plurality of orificci are arranged through the wall of said lumen, both proximally adjacent and distally adjacent said balloon at the distal end of said shaft.

23. A dilatation catheter as recited in claim 21, wherein said acutely disposed opening has a flexible flap arranged thereover and within said lumen, to provide an obstruction therewithin, said flap acting as a valve means with respect to said opening.

24. A dilatation catheter as recited in claim 18, wherein said means for converting said catheter between an "over-the-wire" mode and a "rapid-exchange" mode comprises an acutely disposed slit arranged through the sidewall of said catheter shaft, creating a flexible flap which is bendable to establish an opening in the wall for passage of a guidewire therethrough.

25. A dilatation catheter as recited in claim 18, wherein said means for converting said catheter between an "over-the-wire" mode and a "rapid exchange" mode comprises a longitudinal slot disposed through the sidewall of said catheter shaft, and into said third lumen, for passage of a guidewire therethrough when said slot is flexed apart.

26. A method of performing coronary angioplasty dilatation for opening a constriction in an artery of a patient, comprising the steps of:

providing an elongated guidewire having distal and proximal ends and a dilatation catheter comprising a shaft having a distal and a proximal end, with an elongated expandable balloon disposed about its distal end, a first lumen with a closed distal end arranged therein proximal to said balloon, a second lumen in said shaft open at its proximal end and in fluid communication at its distal end with said balloon, and a third lumen extending the length of said shaft and open at each end thereof, said third lumen having means for converting said catheter between an over-the-wire mode and a rapid-exchange mode, said means for converting said catheter comprising an obstructed opening through the side wall of said lumen proximal of said balloon, said first lumen having a stiffening mandrel therein, the distal end of which extends in said first lumen distal of said obstructed opening;

inserting said guidewire into the vessel system of a patient;

positioning said catheter over the proximal end of said guidewire so that said guide wire is in a sliding fit within said third lumen of said shaft;

advancing said guidewire proximally through said third lumen; and bending said catheter shaft so to as lift said obstruction from said opening in the side of said third lumen to cause the proximal end of said guidewire to exit out the side of said third lumen and extend externally thereof to the proximal end of said catheter, while positioning said balloon within a vessel obstruction.

27. A method of performing coronary angioplasty dilatation as recited in claim 26, including the step of:

perfusing body fluid into said third lumen through a plurality of orificii adjacent said balloon, subsequently perfusing body fluid out of said third lumen on the other end of said balloon.

28. A method of performing coronary angioplasty dilatation as recited in claim 27, including the steps of:

withdrawing said catheter shaft from the patient sufficient to bring the proximal end of said guidewire into juxtaposed correspondence with the side opening in said third lumen;

straightening said catheter shaft at the location of said side opening in said third lumen; and advancing the proximal end of said guidewire through the proximal balance of said third lumen while advancing said catheter shaft back into the vessel system of the patient.

29. A convertible dilatation catheter assembly suitable for performing dilatation procedures within a patient's body comprising:

a) an elongated catheter body having proximal and distal end, a first lumen adapted to receive a guidewire and extending within the catheter body to the distal end thereof and a second lumen adapted to direct inflation fluid therethrough and extending within the catheter body to a distal portion thereof;

b) an inflatable member on a distal portion of the catheter body having an interior in fluid communication with the second lumen;

c) a first guidewire port in the catheter body being located at or near the proximal end of the catheter body and being in communication with said first lumen that is adapted to receive a guidewire;

d) a second guidewire port in the catheter body being spaced from the proximal end of the inflatable member that is on the distal portion of the catheter body and a substantial distance from the proximal end of the catheter body and being in communication with the first lumen that is adapted to receive a guidewire;

e) a third guidewire port in the distal end of the catheter body distal to the inflatable member which is in communication with the first lumen that is adapted to receive a guidewire;

f) a guidewire disposed in rapid exchange mode passing through said second guidewire port, such that a substantial portion of the length of said guidewire is located outside and alongside of said catheter body proximally of said second guidewire port and a portion of said guidewire extends inside said first lumen distally of said second guidewire port and emerges from said third guidewire port;

g) said first lumen being constructed to receive a guidewire in over-the-wire mode, extending from said first guidewire port to said third guidewire port, and h) means on the proximal end of the catheter body to direct inflation fluid to the interior of the inflatable member through the inflation lumen.

30. The assembly of claim 29 wherein said guidewire port is located between about 15 to 35 cm from said inflatable member.

31. The dilation catheter assembly of claim 29 wherein said catheter is constructed as an angioplasty catheter and said guidewire is constructed as an angioplasty guidewire.

32. A method of performing, with a guidewire and catheter, an intravascular procedure within a patient comprising:
  (a) providing an intravascular catheter that is convertible between rapid exchange and over the wire modes of use which includes:
    an elongated catheter body having proximal and distal ends, a guidewire-receiving inner lumen extending within the catheter body from the proximal end to the distal end thereof,
    a procedure-performing formation disposed on the distal portion of the catheter body,
    a first guidewire port in the catheter body being at the proximal end of the catheter body and being in communication with the guidewire-receiving inner lumen,
    a second guidewire port in the catheter body spaced proximally of the procedure-performing device and a substantial distance from the proximal end and being in communication with the guidewire-receiving inner lumen, and
    a third guidewire port in the distal end of the catheter body which is in communication with the guidewire-receiving inner lumen,
  (b) positioning said convertible catheter and guidewire in the vascular system of a patient, with said guidewire disposed within the distal portion of the guidewire-receiving inner lumen and with the distal end thereof extending out the third guidewire port into the patient's vascular system and the proximal portion of said guidewire extending out the second guidewire port and proximally along said catheter body.

33. The method of claim 31 wherein said procedure performing formation is a dilatation balloon and said procedure is angioplasty dilatation for opening a constriction in a blood vessel.

34. The method of claim 32 comprising, during said procedure, converting said catheter to said over-the-wire mode.

35. The method of claim 32 comprising:
  while leaving said guidewire within the vessel, removing said catheter from the body and exchanging for another catheter which is placed into said vessel over said guidewire.

36. A catheter for performing an intravascular procedure within a patient, comprising:
  a catheter body having a distal and a proximal end, with a procedure performing formation disposed about its distal end,
  a guidewire lumen extending the length of said catheter body and open at proximal and distal ends thereof, said guidewire lumen having means for converting said catheter between an over-the-wire mode and a rapid exchange mode which comprises a guidewire receiving opening through the side wall of said lumen proximal of said procedure performing formation, and
  a flap in the region of said opening having one end attached to said catheter body and a free end that can be positioned to produce an obstruction.

37. The catheter of claim 35 wherein said flap is positioned to obstruct said opening.

38. The catheter of claim 35 wherein said flap is positioned to obstruct said guidewire lumen and cause diversion of a guidewire inserted in said distal end to cause it to exit through said opening.

39. The catheter of claim 37 wherein said one end of said flap is attached proximally of said opening.

40. The catheter of claim 38 wherein said flap is movable between a position to obstruct said guidewire lumen and cause diversion of a guidewire inserted in said distal end to cause it to exit through said opening and a position to obstruct said opening.

41. The catheter of claim 35 wherein said one end of said flap is attached distally of said opening and said free end is positionable outwardly to allow free passage through said opening.

42. A catheter for performing a procedure in a blood vessel of a patient, said catheter bring convertible between rapid exchange and over the wire modes of use, said catheter comprising:
  a shaft having a distal and a proximal end, with a procedure-performing formation disposed about its distal end,
  a guidewire lumen within and extending the length of said shaft and open at each end thereof, said guidewire lumen having means for converting said catheter between and over-the wire mode and a rapid exchange mode which comprises a guidewire-passing opening through the side wall of said lumen proximal of said procedure performing formation,
  said catheter further including a removable stiffening element disposed in said guidewire lumen and extending to a region proximal of said opening, said stiffening element being removable to convert said catheter for over-the-wire mode use.

43. The catheter of claim 42 wherein said stiffening element comprises a removable wire stylet.

44. The catheter of claim 42 in combination with a guidewire in the rapid exchange mode wherein said guidewire extends through said opening and occupies said guidewire lumen from said opening to said distal end of said catheter, and said removable stiffening element is a stylet in said guidewire lumen that extends to a position proximal of said opening.

45. The catheter of claim 42 including a further stiffening element extending past and beyond said opening and terminating proximal of said procedure-performing formation.

46. The catheter of claim 45 wherein said removable stiffening element comprises a wire stylet and said further stiffening element is a wire of smaller diameter than said wire stylet.

47. The catheter of claim 46 wherein said wire is positioned in a separate lumen, parallel to said guidewire lumen.

48. The catheter of claim 45 wherein said shaft comprises a multi-lumen extrusion including a substantially round lumen forming said guidewire lumen in which said removable stiffening element is disposed and a narrower lumen in which said further stiffening element in the shape of a wire is disposed.

49. A catheter for performing a procedure in a blood vessel of a patient, said catheter bring convertible between rapid exchange and over the wire modes of use, said catheter comprising:
  a shaft having a distal and a proximal end, with a procedure-performing formation disposed about its distal end,
  a guidewire lumen within and extending the length of said shaft and open at each end thereof, said guidewire lumen having means for converting said catheter between an over-the-wire mode and a rapid exchange mode which comprises a guidewire-passing opening through the side wall of said lumen proximal of said procedure performing formation, said shaft comprising a multi-lumen extrusion including a substantially round lumen forming said guidewire lumen and a narrower lumen in which a stiffening element is disposed, said stiffening element extending past and beyond said opening and terminating proximal of said procedure-performing formation.

50. The catheter of claim 48 or 49 wherein said narrower lumen is of crescent shape.

51. The catheter of claim 42 or 49 wherein said stiffening element is axially adjustable in the lumen in which it resides to vary stiffness along the length of said catheter.

52. The catheter of claim of 32 or 49 wherein said stiffening element is nitinol.

53. A readily exchangeable dilation catheter suitable for performing angioplasty procedures comprising:

a) an elongated catheter body having proximal and distal ends, a first lumen adapted to receive a guidewire and extending within the catheter body to the distal end thereof and a second lumen adapted to direct inflation fluid therethrough and extending within the catheter body to a distal portion thereof;

b) an inflatable member on a distal portion of the catheter body having an interior in fluid communication with said second lumen;

c) a first guidewire port in the catheter body being located at or near the proximal end of the catheter body and being in communication with said first guidewire-receiving lumen;

d) an elongated slot forming a flexible openable orifice serving as a second guidewire port in the catheter body and being in communication with said first guidewire-receiving lumen;

e) a third guidewire port in the distal end of the catheter body distal to the inflatable member, and in communication with the said first guidewire-receiving lumen; and f) means on the proximal end of the catheter body to direct inflation fluid to the interior of the inflatable member through the inflation lumen.

54. The catheter of claim 53 in combination with a guidewire disposed in rapid exchange mode passing through said second guidewire port, such that a substantial portion of the length of said guidewire is located outside and alongside of said catheter body proximally of said second guidewire port and a portion of said guidewire extends inside said first lumen distally of said second guidewire port and emerges from said third guidewire port, said first lumen being constructed to receive a guidewire in over-the-wire mode, extending from said first guidewire port to said third guidewire port.

55. A method of performing, with a guidewire and catheter, an intravascular procedure within a patient comprising:

(a) providing an intravascular catheter that is convertible between rapid exchange and over the wire modes of use which includes:

an elongated catheter body having proximal and distal ends, a guidewire-receiving inner lumen extending within the catheter body from the proximal end to the distal end thereof, a procedure-performing formation disposed on the distal portion of the catheter body, a first guidewire port in the catheter body being at the proximal end of the catheter body and being in communication with the guidewire-receiving inner lumen, a second guidewire port in the catheter body spaced proximally of the procedure-performing device and a substantial distance from the proximal end and being in communication with the guidewire-receiving inner lumen, and a third guidewire port in the distal end of the catheter body which is in communication with the guidewire-receiving inner lumen, (b) positioning said convertible catheter and guidewire in the vascular system of a patient, with said guidewire disposed within the distal portion of the guidewire-receiving inner lumen and with the distal end thereof extending out the third guidewire port into the patient's vascular system and the proximal portion of said guidewire extending out the second guidewire port and proximally along said catheter body; and (c) disposing said catheter in the patient's body under conditions permitting perfusion of blood through said guidewire lumen past said procedure performing formation.

56. A dilatation catheter for performing angioplasty procedures within a patient's coronary artery having a relatively long proximal section which is adapted to remain within a guiding catheter during the angioplasty procedure and a relatively short distal section which is adapted to extend out of the distal end of the guiding catheter during the angioplasty procedure, the dilatation catheter comprising:

a) an elongated catheter shaft which includes an elongated inner tubular structure which has a distal end, a distal guidewire port in the distal end and a guidewire receiving inner lumen extending within the inner tubular structure to the guidewire port in the distal end and an elongated outer tubular structure which is disposed about the inner tubular structure and defines therewith at least one further lumen;

b) an inflatable member on a distal portion of the catheter shaft having a distal end secured to the distal end of the inner tubular structure and an interior which is in fluid communication with a said further lumen between the inner and outer tubular structures;

c) a reinforcing mandrel disposed within a said further lumen between the inner and outer tubular structures which has a relatively long proximal section and a relatively short, distal section which has a smaller diameter than the diameter of the proximal section and which extends into the distal portion of the catheter but terminating proximal to the inflatable member.

57. The dilatation catheter of claim 56 including a guidewire slidably disposed within the guidewire receiving inner lumen.

58. The dilatation catheter of claim 56 wherein the catheter has a proximal end and the mandrel is secured within an adapter mounted on the proximal end of the catheter.

59. The dilatation catheter of claim 56 wherein said mandrel comprises nitinol.

60. The dilatation catheter of claim 56 wherein said mandrel comprises stainless steel.

61. The dilatation catheter of claim 56 wherein the distal section of said mandrel lies loosely within its respective lumen.

62. The dilatation catheter of claim 56 further comprising a guidewire-passing side port in the distal section of said catheter shaft communicating with the guidewire receiving lumen, wherein said mandrel extends from the proximal end of said dilatation catheter to a location past and beyond said side opening.

63. The dilatation catheter of claim 56 wherein there are two of said further lumens for respectively receiving said mandrel and communicating with said inflatable member for inflation.

64. The dilatation catheter of claim 63 wherein said lumen receiving said mandrel is closed immediately proximal of said inflatable member.

65. The dilatation catheter of claim 56 wherein said mandrel is adjustably locked in the vicinity of the proximal end of the catheter.

* * * * *